(12) United States Patent
Walsh et al.

(10) Patent No.: US 9,365,812 B2
(45) Date of Patent: Jun. 14, 2016

(54) SYSTEMS AND METHODS FOR BIO-MASS ENERGY GENERATION

(71) Applicant: GROW ENERGY, INC., Redondo Beach, CA (US)

(72) Inventors: John J. Walsh, Redondo Beach, CA (US); Robert P. Geiger, Redondo Beach, CA (US)

(73) Assignee: GROW ENERGY, INC., Redondo Beach, CA (US)

(*) Notice: Subject to any disclaimer, the term of this patent is extended or adjusted under 35 U.S.C. 154(b) by 0 days.

(21) Appl. No.: 14/601,116

(22) Filed: Jan. 20, 2015

(65) Prior Publication Data

US 2015/0132839 A1 May 14, 2015

Related U.S. Application Data

(63) Continuation of application No. PCT/US2013/051130, filed on Jul. 18, 2013.

(60) Provisional application No. 61/674,296, filed on Jul. 21, 2012.

(51) Int. Cl.
| | |
|---|---|
| *C12M 1/00* | (2006.01) |
| *F24J 2/02* | (2006.01) |
| *F24J 2/06* | (2006.01) |
| *F24J 2/42* | (2006.01) |
| *F24J 2/00* | (2014.01) |

(52) U.S. Cl.
CPC ............ *C12M 21/02* (2013.01); *C12M 31/08* (2013.01); *F24J 2/02* (2013.01); *F24J 2/067* (2013.01); *F24J 2/42* (2013.01); *F24J 2002/003* (2013.01); *Y02E 10/40* (2013.01)

(58) Field of Classification Search
CPC .......... C12M 21/02; C12M 31/08; F24J 2/04; Y02E 10/44
USPC ........................................................ 435/292.1
See application file for complete search history.

(56) References Cited

U.S. PATENT DOCUMENTS

| 5,614,378 A * | 3/1997 | Yang ................. C12M 21/02 435/292.1 |
| 2007/0264708 A1* | 11/2007 | Bayless et al. ............. 435/292.1 |
| 2009/0047722 A1 | 2/2009 | Wilkerson |
| 2010/0210001 A1 | 8/2010 | Seyfried |
| 2011/0174730 A1* | 7/2011 | Chong ................. C02F 3/08 210/602 |

FOREIGN PATENT DOCUMENTS

| JP | 06-064577 A | 3/1993 |
| JP | 05-244932 A | 9/1993 |
| KR | 10-0897019 B1 | 5/2009 |
| WO | 2011-035166 A1 | 3/2011 |

OTHER PUBLICATIONS

International Search Report and Written Opinion issued in International Application No. PCT/US2013/051130 on Oct. 18, 2013.

* cited by examiner

*Primary Examiner* — Nathan Bowers
*Assistant Examiner* — Timothy Barlow
(74) *Attorney, Agent, or Firm* — Kilpatrick Townsend & Stockton LLP

(57) ABSTRACT

A closed loop system for generating energy is described herein. The closed loop system can include a solar collector, a tank, and the combustor. The solar collector can collect electromagnetic energy from a light source including, the sun. This electromagnetic energy can be transported from the solar collector to the tank via a light guide. The tank is illuminated with electromagnetic energy and biomass grows in the tank. The biomass is transported to the combustor and burned to generate heat energy. This heat energy can be used to generate electricity.

11 Claims, 9 Drawing Sheets

One embodiment of the distribution of irradiance through the PBR as a function of depth along the length of the PBR when electromagnetic energy is provided at one of the top and bottom of the PBR.

One embodiment of the distribution of irradiance through the PBR as a function of depth along the length of the PBR when electromagnetic energy is provided at both the top and bottom of the PBR.

SYSTEMS AND METHODS FOR BIO-MASS ENERGY GENERATION

CROSS-REFERENCES TO RELATED APPLICATIONS

This application is a continuation of International Application No. PCT/US2013/051130, filed on Jul. 18, 2013, and entitled SYSTEMS AND METHODS FOR BIO-MASS ENERGY GENERATION, which is a non-provisional of U.S. Provisional Application No. 61/674,296, filed on Jul. 21, 2012, and entitled BIOFUEL GENERATOR USING ALGAE, the entirety of which are incorporated by reference herein.

FIELD OF THE INVENTION

The present invention relates to devices which produce electrical power in one or more phases.

BACKGROUND OF THE INVENTION

Solar energy is the predominant source of energy for all life forms on earth. Certain life forms have learned to utilize solar energy directly in the very efficient process known as photosynthesis; algae is one such creature that converts solar energy to oil at an incredibly rapid rate.

Collecting solar energy has been a topic of research largely centered on photovoltaic cells and much technological advancement has resulted; one such technology is the Luminescent Solar Concentrator (LSC). This technology provides a cheap method of concentrating solar radiation, both direct and diffuse, without a tracking system. Although this technology is very well developed it is still not economically viable for photovoltaic applications due to photovoltaic related costs.

A large issue for solar technologies is that they have an extensive reliance on the collective power grid because they are unable to effectively store the energy it generates. In addition to the expense associated with photovoltaics (PV), grid dependency results in a decrease in return on investment for consumers, and a decrease in incentive for adoption due to its overall lack of economic viability and reliance on the power utility. Their inability to produce electricity on demand is a major drawback. Indeed, electricity peak demands occur in the morning and at the end of afternoons while photovoltaic peak load capacity is observed at the beginning of the afternoon. This leads to either using electricity storing systems, like lead-acid batteries, that can be expensive (120$/KWh), or selling the electrical production on the grid. This potential massive selling of electricity can lead to congestion in electrical transmission lines and to a lower price of electricity, that can limit the return on investment for the producer.

Without cost effective storage methods, the adoption of grid dependent systems are limited to a low capacity of the power grid because of the on-grid system's rapid fluctuation of power supply to the grid during the day and at night. To maintain grid balance and to avoid frequent grid blowouts a storage method is used, but without economical energy storage it makes it difficult for large penetration of PV technology. Due to this reliance, regardless of a homeowner's conversion to existing solar photovoltaic technologies, individuals and businesses are subject to market influence of energy costs, power utility regulations, and limitations of solar integration with the current collective power infrastructure. All of these factors make widespread adoption of PV technology difficult One solar technology, biomass, has been explored thoroughly as a cheap alternative source of energy. The technology surrounding this idea is well developed. However biomass utilization is expensive as biomass has historically been transported from the location where it is grown to the location where it is used as an energy source, which transportation can be very expensive. In light of these problems, further advancements in the field of solar technology and biomass are desired.

SUMMARY OF THE INVENTION

Some aspects of the present disclosure provide a growth system. In some embodiments, the growth system can include a solar collector, a tank, and a guide that connects the solar collector and the tank. In some embodiments, the guide can transmit electromagnetic energy collected by the solar collector to the tank, and can, in some embodiments, distribute the transmitted electromagnetic energy throughout the tank.

In some embodiments, the guide can include a first end, a second end, and a sidewall extending between the first end and the second end. In some embodiments, the guide can further include a guide portion and a dispersion portion. In some embodiments, the sidewall of the guide portion can retain electromagnetic energy within the guide, and in some embodiments, the sidewall of the dispersion portion can allow electromagnetic energy to exit the guide.

In some embodiments, the growth system can further include a building having a first area that is exposed to direct sunlight during a portion of the day. In some embodiments, the solar collector can be located in and/or on the first area of the building, and in some embodiments, the tank can be located in and/or on a second area of the building.

In some embodiments, the dispersion portion of the guide is located proximate to the tank, and in some embodiments, the dispersion portion of the guide is located inside the tank.

Some aspects of the present disclosure relate to a growth system. In some embodiments, the growth system can include a tank, and a plurality of guides that transmit electromagnetic energy. In some embodiments, the guides extend into the tank, and are placed so as to create a homogenous distribution of the transmitted electromagnetic energy in the tank.

In some embodiments, the guides can include a first end, a second end, and a sidewall extending between the first end and the second end. In some embodiments, the guide can include a guide portion having a sidewall that retains electromagnetic energy within the guide and a dispersion portion with a sidewall that allows electromagnetic energy to exit the guide. In some embodiments, the dispersion portion of the guide can be located in the tank, and in some embodiments, the dispersion portion of the guide can be located proximate to the tank. In some embodiments, the homogenous distribution of transmitted electromagnetic radiation in the tank can be created by one of, the length of the dispersion portion of the plurality of guides, the number of the plurality of guides, and the spacing of the plurality of guides. In some embodiments, the light guides receive light from the solar collector and channel the received light to the tank, and in some embodiments, the number and/or placement of the plurality guides creates a homogenous distribution of the transmitted electromagnetic energy in the tank. In some embodiments, the growth system can further include a solar collector.

Some aspects of the present disclosure relate to a method of generating energy. In some embodiments, this method can include, for example, illuminating photosynthetic cells located within a growth medium in a closed loop system with collected radiation, concentrating the photosynthetic cells, combusting the concentrated photosynthetic cells, and introducing a byproduct of the combustion of the concentrated photosynthetic cells to the closed loop system.

In some embodiments of the method of generating energy, the radiation is sun light that can be, for example, collected with a solar collector. In some embodiments, the collected sun light can be transmitted from the solar collector to the closed loop system.

In some embodiments, the method of generating energy can further include generating electricity with the heat from the combustion of the concentrated photosynthetic cells. In some embodiments, the combustion of the concentrated photosynthetic cells drives a turbine including, for example, steam turbine to generate electricity, and in some embodiments, the combustion of the concentrated photosynthetic cells drives a Stirling engine to generate electricity.

Some aspects of the present disclosure relate to a method of growing photosynthetic cells. In some embodiments, the method can include collecting radiation with a solar collector, transmitting collected radiation from the solar collector to a tank via a guide connecting the solar collector and the tank, the tank including a growth medium including photosynthetic cells, and illuminating the photosynthetic cells in the tank with the radiation transmitted via the guide.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

Figure 1:
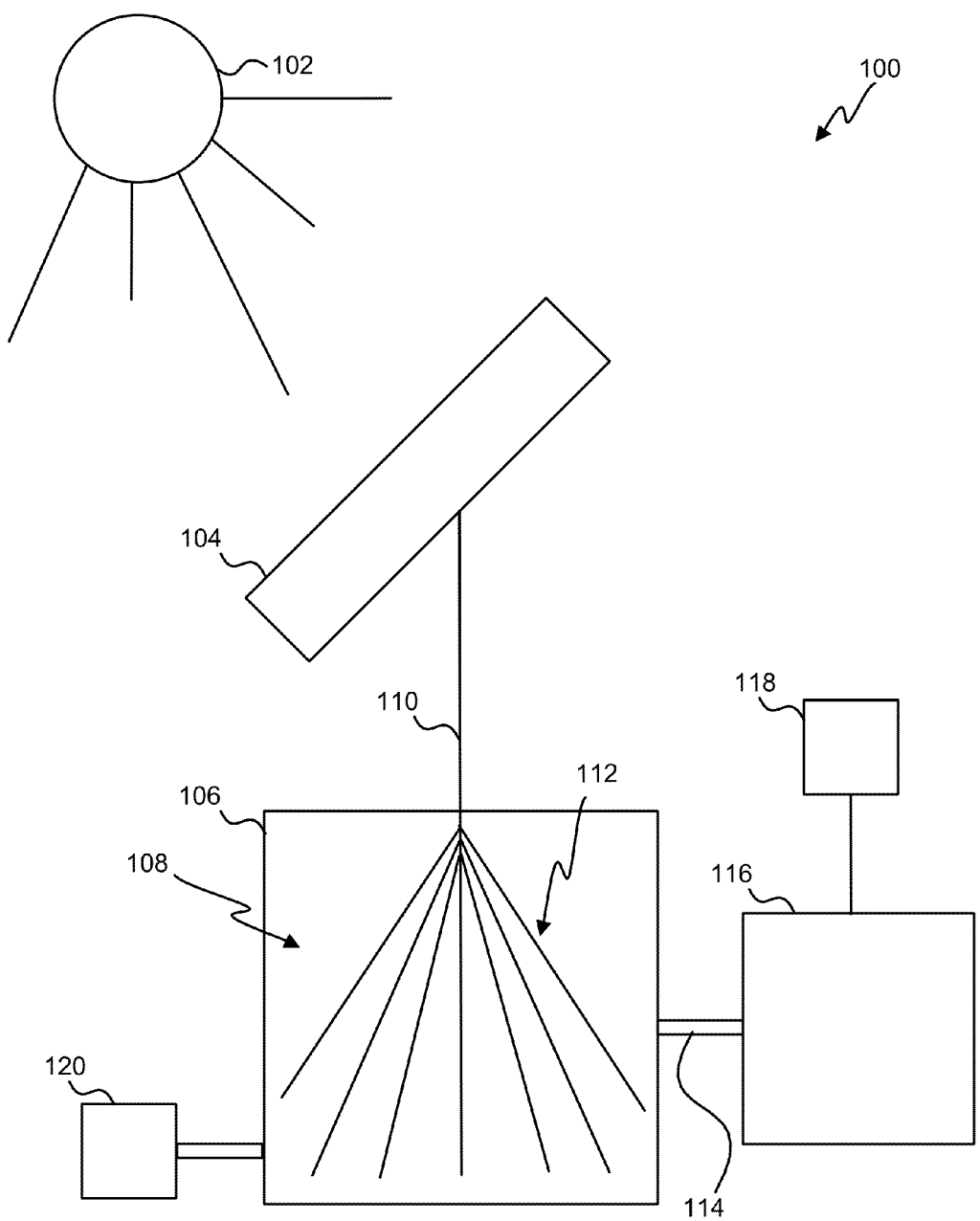
FIG. 1 is a schematic illustration of one embodiment of a biomass energy generation system.

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In some embodiments, a biomass energy generation system can create an environment in which biomass can grow, and can use the grown biomass to generate electricity. The biomass energy generation system can create an environment in which biomass can grow by providing desired physical parameters to encourage growth. These can include, for example, providing light and nutrients to the biomass.

In one aspect, the biomass energy generation system can collect solar energy and provide that energy to biomass, that can be, for example, algae, in a tank. The solar energy can be collected with a solar collector and can be transported from the solar collector to the tank via one or several light guides. The light guide can be arranged to provide a desired light distribution pattern within the tank. In one aspect, for example, this can be performed by creating a dispersion pattern of a plurality of light guides within the tank.

The tank can include sensors that measure environmental parameters of the tank such as the temperature, pH, chemical composition, illumination level, and/or nutrient availability levels. The tank can further include an inlet for a growth medium, which growth medium can include nutrients for the biomass in the tank. The tank can further include an outlet for the growth medium. This outlet can also be used to remove some or all of the biomass from the tank. The tank can additionally include a gas inlet and a gas outlet. In some aspects, the gas inlet can be used to provide gas containing desired chemicals and/or nutrients to the tank and/or to the biomass within the tank.

The biomass energy system can further include a concentrator that can receive the growth medium and biomass from the growth medium outlet and can separate the biomass from the growth medium and/or concentrate the biomass. This concentrated and/or separated biomass can then be combusted to generate heat energy and exhaust gases. The exhaust gases can be provided to the tank to maintain desired chemical and/or nutrient composition within the tank, and the heat energy can be used to, for example, heat water, heat air, and/or to drive a heat engine that can be used to generate electricity.

With reference now to FIG. 1, a schematic illustration of one embodiment of a biomass energy generation system 100 is shown. As discussed above, the biomass energy generation system 100 can be configured to provide light and nutrients to a tank to facilitate the growth of biomass. The biomass can comprise any organism(s) that is combustible. In some embodiments, this organism(s) can be selected based on combustibility, on energy released by combustion, speed of growth, ease of growth, and/or any other desired parameter. In some embodiments, the biomass can comprise algae, and can specifically comprise algae that contain and/or develop a high lipid, oil, and/or hydrocarbon content. In one embodiment, for example, an algae can be selected that has and/or develops a lipid, oil, and/or hydrocarbon bodyweight (wet or dry bodyweight) percent of 10%, 20%, 30%, 50%, 60%, 70%, 80%, 90%, and/or any other or intermediate percent. In one embodiment, for example, the biomass can comprise *Chlorella vulgaris* and/or *Botryococcus Braunii*.

In some embodiments, the biomass can be combusted to generate heat energy which can be used to, for example, heat a room, heat water, and/or be converted to work by, for example, heat engine, which can be converted into electricity.

In some embodiments, the biomass energy generation system 100 can comprise a closed loop system. As used herein, a closed-loop system refers to a system in which the byproducts and/or outputs of biomass energy generation system 100, except for the desired and/or requested energy outputs, are captured and redirected into the biomass energy generation system 100. Thus, for example, combustion byproducts of the biomass energy generation system 100 are captured and redirected into the system and byproducts of the growth and/or generation of biomass are captured and redirected into the system.

As depicted in FIG. 1, the biomass energy generation system 100 is irradiated by a light source 102 which can be, for example, the sun. In some embodiments, all of the electromagnetic energy used by the biomass energy generation system 100 can come from the sun, and in some embodiments, electromagnetic energy received from the sun can be supplemented with electromagnetic energy from another light source 102 to achieve and/or maintain optimal and/or desired growing conditions within the tank.

The biomass energy generation system 100 can include a solar collector 104. In some embodiments, the solar collector 104 can be configured to receive electromagnetic energy (also referred to herein as radiation and/or light) including, for example, both visible and nonvisible light, from the light source 102, concentrate the electromagnetic energy, and provide the concentrated radiation to a light guide.

Figure 1A:
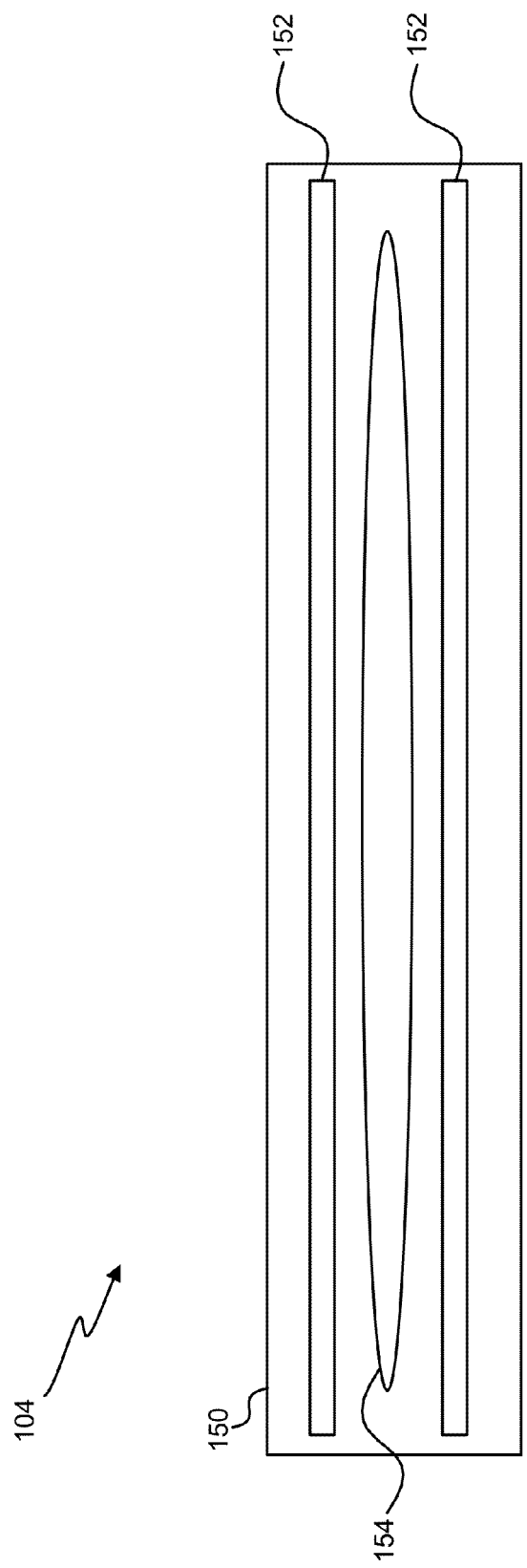
FIG. 1A is a schematic illustration of a luminescent solar concentrator (LSC).

In some embodiments, the solar collector 104 can comprise a luminescent solar concentrator (LSC) 150. The LSC 150 is shown in FIG. 1A. In some embodiments, a LSC 150 can operate by application of total internal reflection and luminescence. In one embodiment, for example, the LSC 150 can comprise alternating parallel thin plates 152 of luminescent and transparent material. In one embodiment, the LSC can comprise a plastic or glass plate that is doped with a luminescent dye, and in one embodiment, the LSC can comprise a luminescent liquid 154 contained between two plates 152. In these embodiments, incoming electromagnetic energy impinges on the surface of the plate, is absorbed by the luminescent material, and reemitted at a longer wavelength. This emitted light is then trapped in the transparent medium by total internal reflection. The combination of the luminescence and the total internal reflection results in the shifting of the wavelength of the electromagnetic energy that impinges on the surface of the plate to a lower wavelength, and the guiding of the electromagnetic energy having a lower wavelength to a desired portion of the LSC.

The solar collector 104 can comprise a variety of shapes and sizes and can be made from a variety of materials. The solar collector 104 will be discussed in greater detail below.

The biomass energy generation system 100 can include a tank 106. The tank 106 can comprise one or several tanks that can perform a variety of functions within the biomass energy generation system 100. In some embodiments, one or several of tanks 106 can be configured to grow biomass and/or to store biomass.

The tank 106 can define a volume. In some embodiments, the volume of the tank 104 can be configured to contain the grown biomass and any growth medium used in connection with the biomass. The tank 106 can comprise a variety of shapes and sizes and can be made from a variety of materials. In some embodiments, for example, the tank 104 can be sized and shaped so as to maximize the internal volume of the tank as compared to the surface area of the tank. In some embodiments, advantageously, the maximization of the internal volume of the tank with respect to the surface area of the tank 104 can decrease the amount of external environmental impact on the contents of the tank 104, and can thereby facilitate maintaining optimal and/or desired environmental conditions within the tank 104.

In some embodiments, the tank 106 can comprise a photobioreactor (PBR) and a storage tank. In some embodiments, the PBR can house the biomass during its growth phase. In some embodiments, the biomass can be irradiated with electromagnetic energy from the light source 102 during its growth phase. This electromagnetic energy can, as discussed above, be collected by the solar collector 104 and transported to the PBR via the light guide 110. The PBR can further receive nutrients to support and/or encourage the growth of the biomass.

In some embodiments, the tank 106 can further include a biomass holding tank. The biomass holding tank can comprise a variety of shapes and sizes and can be made from a variety of materials. In some embodiments, the biomass holding tank can define an internal volume. In some embodiments, this internal volume can be configured to hold biomass after it has completed its growth phase. In some embodiments, the biomass holding tank can be sized to hold sufficient biomass to provide a desired amount of stored energy. In some embodiments, for example, biomass holding tank can be configured to hold sufficient biomass to allow maximum operation the system for desired amount of time without the growth of any new and/or additional biomass. In some embodiments, this amount of time can have any desired length including, for example, 1 hour, 2 hours, 3 hours, 6 hours, 9 hours, 12 hours, 24 hours, 48 hours, 72 hours, 144 hours, 1 month, 2 months, 1 year, and/or any other or intermediate length of time.

In some embodiments, the biomass storage tank can include a sensor configured to monitor the amount of biomass within the biomass storage tank. In some embodiments, the biomass storage tank can be further connected to, for example, the PBR and can receive new and/or additional biomass from the PBR. In some embodiments, the biomass storage tank can be configured to provide biomass to other components of the biomass energy generation system 100.

In some embodiments, the biomass storage tank can be configured to have environmental conditions to maintain the state of the contained biomass and/or further the development of the contained biomass. In one embodiment, the biomass storage tank can be configured to receive light and/or nutrients to maintain the biomass. In one specific embodiment, the biomass storage tank can be configured to be irradiated by electromagnetic radiation collected by the solar collector 104.

In some embodiments, the tank 106 can include one or several input streams and/or outputs streams. These streams can provide nutrients to the biomass contained within the tank 106, move the biomass between the tanks comprising the tank 106, and/or provide any other desired inputs to the tanks 106.

In some embodiments, the tank 106 can contain a growth medium 108. The growth medium can comprise any liquid, gaseous, and/or solid medium that contains the biomass and provides nutrients and/or support to the biomass. The growth medium 108 can comprise a variety of compositions and can be provided in a variety of volumes. In some embodiments, the growth medium 108 can be circulated through the tank 106. In some embodiments, the temperature of the growth medium can be raised or lowered to affect an environmental parameter of the tank, and in some embodiments, one or several nutrients and/or chemicals can be added to the growth medium to affect and/or maintain a desired environmental parameter within the tank 106.

The growth medium can have a variety of compositions. In one embodiment, for example, the growth medium can comprise some or all of the following solutions (see Tables 1-3) in the indicated concentration.

Table 1 presents one embodiment of the Beijerinck Solution.

TABLE 1

Beijerinck Solution (50 ml/l)

| Chemical | Concentration |
|---|---|
| $NH_4Cl$: | 8 g/l |
| $MgSO_4, 7H_2O$: | 2 g/l |
| $CaCl2, 2H2O$: | 1 g/l |

Table 2 presents one embodiment of a Phosphate Buffer Solution.

TABLE 2

Phosphate Buffer Solution (1 ml/l)

| Chemical | Concentration |
|---|---|
| $K_2HPO_4$: | 106 g/l |
| $KH_2PO_4$: | 53 g/l |

Table 3 presents one embodiment of the composition of the Metal Trace Solution.

TABLE 3

Metal Trace Solution (1 ml/l)

| Chemical | Concentration |
|---|---|
| $Na_2EDTA, 2H_2O$ | 50 g/l |
| $ZnSO_4, 7H_2O$: | 22 g/l |
| $H_3BO_3$ | 11.4 g/l |
| $MnCl_2, 4H_2O$ | 5.1 g/l |
| $FeSO_4, 7H_2O$ | 5 g/l |
| $CoCl_2, 6H_2O$ | 1.6 g/l |
| $CuSO_4, 5H_2O$ | 1.16 g/l |
| $(NH_4)_6Mo_7O_{24}, 4H_2O$: | 1.1 g/l |

The biomass energy generation system 100 can further include a light guide 110. In some embodiments, the light guide 110 can be configured to receive radiation from the solar collector 104 and transport the radiation to the tank 106. In some embodiments, for example, the light guide can be configured to transport radiation to the tank 106 and to distribute the radiation throughout the tank 106. In some embodiments, the light guide 110 can comprise a first material and/or first attribute that facilitates the transport of radiation to the tank 106 and a second material and/or attribute that facilitates the distribution of the light in the tank 106. The light guide 110 can comprise a variety of shapes and sizes and can be made from a variety of materials.

Advantageously, the use of a light guide 110 to connect the solar collector 104 and the tank 106 can allow placement of the solar collector 104 and the tank 106 in different locations. In one embodiment in which the biomass energy generation system 100 is used in connection with a structure and/or building, the solar collector 104 can be positioned on a first portion of the structure that is directly exposed to the light source 102 during a portion of a day, and the tank on and/or in a second portion of the structure that can be, for example, remote from the first portion of the structure. In some embodiments, this allows placement of the solar collector 104 on, for example, the roof or on a sunlight exposed exterior wall of the structure, and placement of the tank 106 inside the structure and/or on an external wall that is not exposed to direct sunlight.

In some embodiments, the light guide 110 of the biomass energy generation system 100 can comprise a dispersion array 112. In some embodiments, the dispersion array 112 can be sized and shaped so as to achieve a desired and/or optimal distribution of light throughout the tank 106. In some embodiments, for example, all or portions of the dispersion array 112 can be located within the tank 106. In some embodiments, some, or parts of the dispersion array 112 can comprise the same material and/or attributes of the other portions of the light guide 110, and in some embodiments, some, or parts the dispersion array 112 comprise different materials and/or attributes than the other portions of the light guide 110. The dispersion array 112 can comprise a variety of shapes and sizes, the details of which will be discussed at greater length below.

The biomass energy generation system 100 can further comprise a concentrator 114. In some embodiments, the concentrator 114 can be configured to receive all or portions of the biomass stored within the tank 106 and/or receive all or portions of the growth medium 108 contained within the tank 106 and containing biomass. The concentrator 114 can be configured to determine the concentration of the biomass, compare the determined and/or measured concentration of the biomass to a desired biomass concentration, and, if the measured and/or determined concentration levels do not match the desired concentration levels, the concentrator 114 can be configured to increase the concentration of the biomass by, for example, separating the biomass from the growth medium 108. In some embodiments, for example, the separation can include the mechanical, chemical, electrical, and/or other separation of the biomass from the growth medium 108. In some embodiments, the separation can be performed by, for example, filtration, centrifugation, dehydration, magnetic and/or electrical separation, and/or by any other desired technique.

In some embodiments, this separation process is a solid-liquid type separation. In embodiments in which the biomass is algae, the separation process involves removing small algae cells, which can have, for example, a size ranging between 1-100 µm from a liquid using one or several of a mechanical, chemical, electrical, and/or magnetic technique. These different separation techniques, and the specific application of each of these separation techniques can result in different separation efficiencies. In some embodiments, the separation processes can be performed in single or multiple stages.

In some embodiments, algae separation techniques can be one of the following: flocculation, filtration, flotation, centrifugal sedimentation, dehydration, electrophorectic, dielectrophoretic, electroporation, or the like. In some embodiments, flocculation can include a process whereby solids within the solution including, for example, one or several algae cells, form clusters which then fall out of solution. In some embodiments, this can be induced, for example, naturally, chemically, and/or electrically. In one embodiment, for example, the limitation of carbon dioxide within the tank 106, and thereby the limitation of carbon dioxide supplied to the biomass, and specifically to the algae can initiate autoflocculation.

In some embodiments, filtration can include a process which exploits the size of the solids to screen the solids from the liquid, and in some embodiments, the flotation can include a process that exploits hydrophobic and hydrophilic properties of the solids in order to induce separation. Centrifugal sedimentation is a process which uses the density difference between the solids and liquids in order to promote separation, and dehydration is a process whereby liquid is separated from the biomass, and specifically, whereby water is separated from the biomass, including, for example, the algae, via the application of heat to the mixture of liquid and biomass. In some embodiments, for example, electrophoretic separation is a process that can separate biomass from the liquid by exploiting either a naturally occurring and/or induced charge of the solids. In such an embodiment, an external electric field can be established which can cause particle movement, and thereby separation of the biomass from the liquid. In some embodiments, dielectrophorectic separation can use the differences in permittivities of the materials, by application of an electric field, to induce separation of the biomass from the liquid. In some embodiments, electroporation can use the presence of an electric field to cause an opening of the cell wall; which results in a change in the properties of the cell and thereby leads to automatic separation. In some embodiments, after the biomass, and specifically, after the algae are separated from the growth medium 108 the growth medium 108 can be recycled to support further biomass growth.

In some embodiments, the concentrator can be further configured to dewater the biomass. In some embodiments, the dewatering of the biomass can be performed as a part of the separation process, and in some embodiments, the dewatering can be performed separate from the separation process. In some embodiments, the dewatering can include the dehydration of the biomass and/or the separation of the lipid, oil, and/or hydrocarbon from other components of the biomass. In some embodiments in which the lipid, oil, and/or hydrocarbon are separated from other components of the biomass, this separation can occur via direct oil excretion, which can be engineered, for example, by cyanobacteria. The separated oil can be recovered via decantation, and the biomass can be used for new and/or future lipid, oil, and/or hydrocarbon production.

In one embodiment, for example, the combination of biomass and liquid, referred to as a stream, can be received from the tank 106. In some embodiments, the concentration of the stream can be determined, and separation of the stream can be performed. In some embodiments in which the biomass concentration of the stream is too high, the stream can be diluted, and in some embodiments in which the biomass concentration of the stream is too low, a portion of the liquid in the stream can be removed.

In some embodiments, the biomass energy generation system 100 can include combustor 116. The combustor 116 can be configured to combust biomass. The combustor 116 can comprise a variety of types and shapes and sizes, and can be made for a variety of materials. In one embodiment, for example, the combustor 116 can comprise a fluidized bed combustor. In such an embodiment, the combustor 116 can suspend portions of the biomass in jets of air. In such an embodiment, the combustor can be connected to a fuel source and to an oxidizer source. The fuel source can comprise the biomass. The biomass can be mixed with the oxidizer, including, for example, a solid, liquid, and/or gaseous oxidizer, from the oxidizer source and suspended within an air jet. The biomass can be combusted while suspended within the air jet.

In some embodiments, the combustor 116 can comprise sensors configured to monitor the temperature of the combustion and adjust the supply of fuel and/or of oxidizer based on the measured temperature combustion. Similarly, in some embodiments, the combustor 116 can comprise sensors configured to measure and/or detect combustion byproducts and to adjust amounts of fuel and/or oxidizer flowing to the combustor 116 based on these combustion byproducts.

In one embodiment, the combustor can comprise a sensor configured to measure the temperature of the incoming fuel and/or oxidizer. In some embodiments, the combustor 116 can further comprise a heat exchanger configured to warm and/or cooled a fuel and/or oxidizer to a desired temperature and/or to within a desired temperature range. Advantageously, in some embodiments, the heat exchanger can facilitate efficient combustion, and thereby increase the efficiency of the biomass energy generation system 100.

In some embodiments, the combustor 116 can include an exhaust. The exhaust can transport combustion byproducts from the combustor 116. In some embodiments, these combustion byproducts can comprise, for example, carbon dioxide and steam. In some embodiments, energy and these byproducts can be used to heat air and/or water, or can be used to drive a heat engine which can be used to generate electricity. In some embodiments, the exhaust products can be recirculated through the biomass energy generation system 100 including, for example, through the growth medium 108 to increase the concentration of, for example, carbon dioxide within the growth medium 108 and/or to increase the temperature of the growth medium 108.

The biomass energy generation system 100 can further comprise a generator 118. In some embodiments, the generator 118 can include, for example, a heat engine that is configured to convert heat energy generated by the combustor 116 into work.

The heat engine can comprise a variety of shapes and sizes, can be made from a variety of materials, and can comprise a variety of types. In some embodiments, for example, the heat engine can comprise a turbine, a steam turbine, a Stirling engine, and/or any other desired type of heat engine. In one embodiment, the heat engine can comprise a free-piston Stirling engine.

In some embodiments, the generator 118 can be configured to generate electricity. The generator can comprise a variety of shapes and sizes, can be made from a variety of materials, and can be a variety of types. In some embodiments, the generator 118 can be mechanically connected with the heat engine. In one specific embodiment, the generator 118 can be an integral component of the heat engine. Specifically, in one embodiment in which the heat engine is a Stirling engine, the generator 118 can comprise a permanent magnet linear alternator. Advantageously, components of the permanent magnet linear alternator can be built into the piston of the heat engine such that the movement of the piston of the heat engine is sufficient to generate electricity. This advantageously eliminates any mechanical linking components between the generator 118 and the heat engine, and thereby decreases and/or minimizes frictional losses and increases the efficiency of the generator 118.

In some embodiments, the biomass energy generation system 100 can further include a feed system 120. In some embodiments, the feed system 120 can be configured to determine the chemical composition of the growth medium 108 and/or environmental condition of the tank 106, and adjust the chemical composition the growth medium 108 and/or the environmental condition of the tank 106 to a desired level. In some embodiments, for example, the algae combustion products contain nutrients as well which are combined with the recycle stream and fed back to the beginning of the process. In some embodiments, the feed system 120 can provide some or all of the solutions outlined in Tables 1-3 to the tanks 106.

Figure 2:
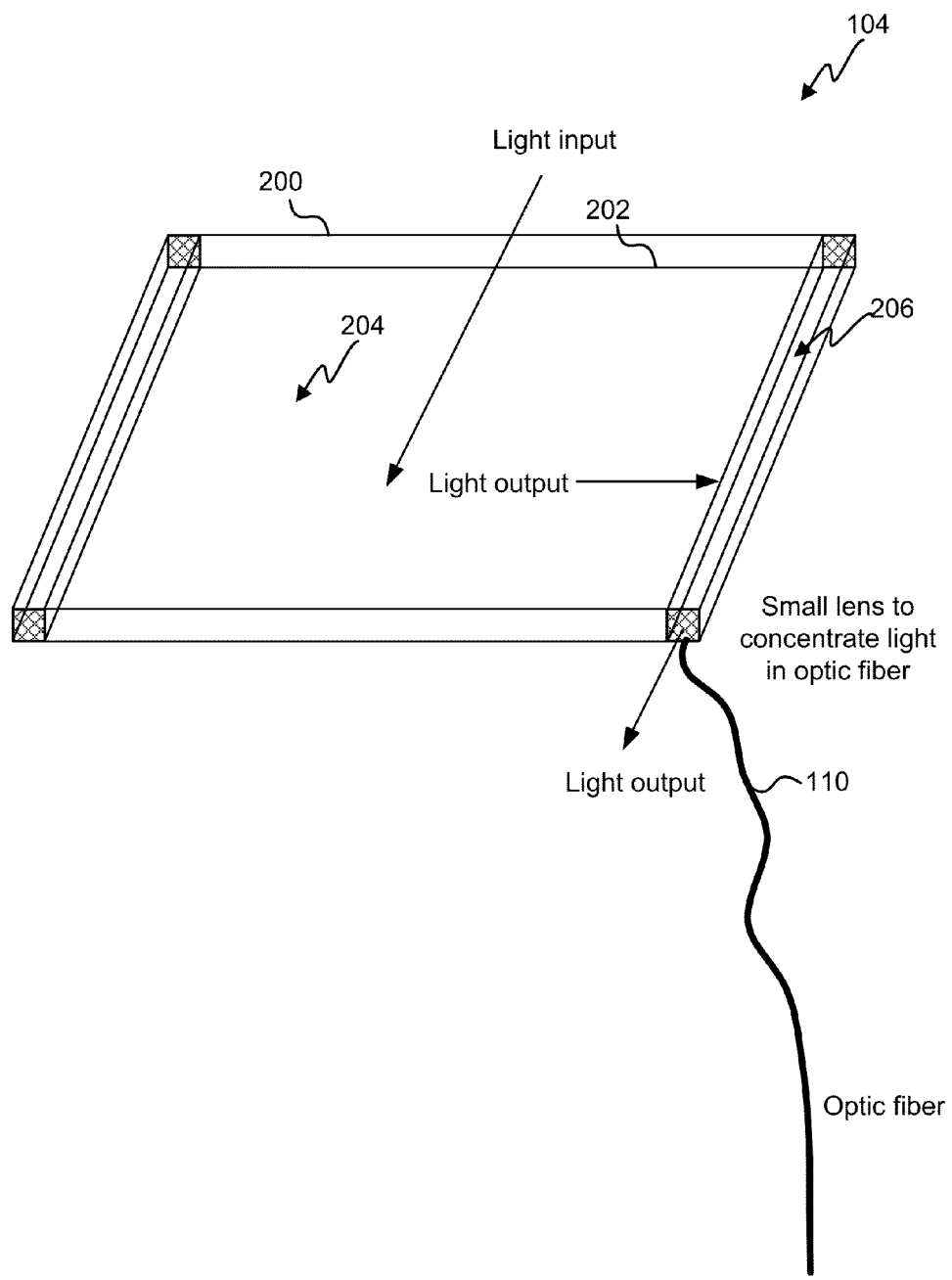
FIG. 2 is a perspective view of one embodiment of a solar collector.

With reference now to FIG. 2, a perspective view of one embodiment of a solar collector 104 is shown. The solar collector 104 can be configured to collect and/or concentrate both direct and indirect electromagnetic energy from the light source 102. In some embodiments, the solar collector 104 can comprise a top 200, a bottom 202, a collection portion 204, and a concentration portion 206. The solar collector 104 can comprise a variety of shapes and sizes and can be made from a variety of materials.

In some embodiments, the top 200 of the solar collector 104 can comprise a luminescent material. In some embodiments, this material can comprise one or several organic dyes and/or quantum dots that can be configured to absorb electromagnetic energy and admit electromagnetic energy. In some embodiments, the one or several organic dyes and/or quantum dots can be arranged so that their emitted electromagnetic energy is guided to the concentration portion 206 of the solar collector 104. In some embodiments, the one or several organic dyes and/or quantum dots can be arranged so that their emitted electromagnetic energy passes into the volume between the top 200 and the bottom 202 of the solar collector 104. In some embodiments, for example, a material can be located between the top 200 and the bottom 202 of the solar collector 104 that is capable of receiving electromagnetic energy, and then, via total internal reflection, retaining all or portions of the receiving electromagnetic energy. This retained electromagnetic energy is then guided to the concentration portion 206 of the solar collector 104 wherein is channeled into the light guide 110.

Figure 3:
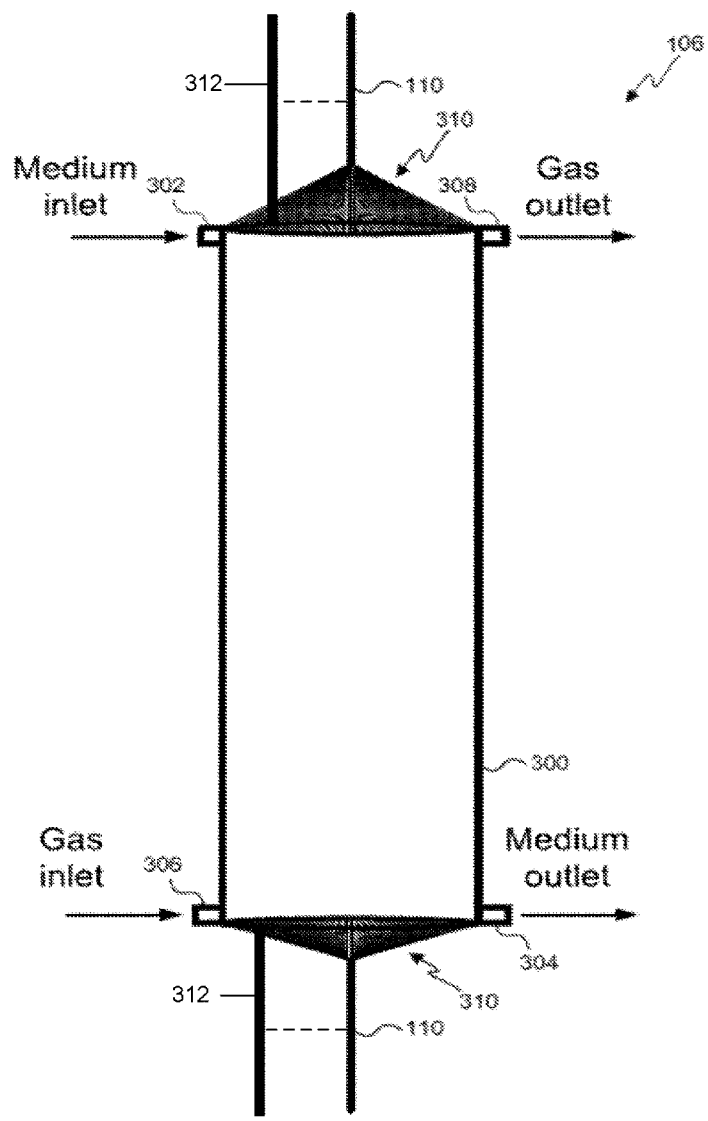
FIG. 3 is a schematic illustration of one embodiment of a tank.

With reference now to FIG. 3, a schematic illustration of one embodiment of a tank 106 is shown. The tank 106 comprises a PBR 300. The PBR 300 can comprise a variety of shapes and sizes and can be made from a variety of materials. In some embodiments, the shapes and sizes and materials of the PBR 300 are limited by the desired volume of growing biomass to be stored within the PBR 300, the desired amount of illumination of the PBR 300, and/or the desired amount of produced energy. In the embodiment depicted in FIG. 3, the PBR 300 is cylindrical. In some embodiments, the PBR 300 can be shaped so as to maximize the ratio of the volume of the PBR 300 to the surface area of the PBR 300.

The PBR 300 can comprise a medium inlet 302 configured to allow fluid including, for example, growth medium 108, to pass into the PBR 300, a medium outlet 304 configured to allow fluid including, for example, growth medium 108 and any therein suspended biomass to pass out of the PBR 300, gas inlet 306 configured to allow gas to pass into the PBR 300, and gas outlet 308 configured to allow gas to pass out of the PBR 300. In some embodiments, gas exiting the PBR 300 via the gas outlet 308 can be provided to the combustor 118, and be combusted with the biomass.

As further seen in FIG. 3, the PBR 300 can connect to the light guide 110. In some embodiments, for example, the PBR 300 can connect to one or several light guides 110 which can enter into the PBR 300 at different locations. In some embodiments, for example, connection of the PBR 300 with a single light guide 110 may not result in a desired level of homogenous illumination within the PBR 300. In such an embodiment, the homogeneity of the illumination of the PBR 300 may be increased by a connection of additional light guides 110, such as light guides 312 shown in FIG. 13 to the PBR 300. In one embodiment, for example, a first light guide 110 may be connected to a first side of the PBR 300 such as, for example, the top of the PBR 300, and the second light guide 312 may be connected to an opposite, second side of the PBR 300 such as, for example, the bottom of the PBR 300.

In some embodiments, for example, the homogenous illumination of the PBR 300 is facilitated by a first portion of the light guide 110 and a second portion of the light guide 110. In some embodiments, the first portion of the light guide 110 can be configured to direct electromagnetic radiation to the PBR 300 from the solar collector 104, and the second portion of the light guide 110 can be configured to distribute the light from the solar collector 104 throughout the PBR 300. In some embodiments, the second portion of the light guide 110 can be partially or completely located within the PBR 300, and in some embodiments, the second portion of the light guide 110 can be partially and/or completely located proximate to the PBR 300.

In some embodiments, the first portion of the light guide 110 can comprise a first material. In one embodiment, for example, the first portion of the light guide can comprise glass optic fibers which can be, for example, made from silica and can have a light-loss of less than 20 dB/Km, less than 10 dB/Km, less than 5 dB/Km, less than 1 dB/Km, less than 0.5 dB/Km, less than 0.2 dB/Km, less than 0.1 dB/Km, less than 0.001 dB/Km, less than 0.0001 dB/Km, and/or any other or intermediate value. In one embodiment, the first portion of the light guide 110 can comprise a material having a light-loss of between 1 dB/Km and 0.2 dB/Km.

In some embodiments, the second portion of the light guide 110 can comprise a second material. In one embodiment, for example, the second portion of the light guide 110 can comprise a plastic optic fiber such as, for example, polymethyl methacrylate (PMMA). In some embodiments, the second portion of the light guide 110 can have a light-loss that is larger than the light-loss of the first portion of the light guide 110. In one embodiment, for example, the second portion of the light guide 110 can have a light-loss of approximately 100,000 dB/Km, 50,000 dB/Km, 20,000 dB/Km, 10,000 dB/Km, 5,000 dB/Km, 1,000 dB/Km, 500 dB/Km, 100 dB/Km, and/or any other or intermediate value. In one embodiment in which the second portion of the light guide 110 has a light-loss of 10,000 dB/Km, in a 2 meter long piece of the second portion of the light guide 110, 99% of incident photon flux density is laterally lost.

In some embodiments, the second portion of the light guide 110 can comprise a plurality of sub light guides 310. In some embodiments, the sub light guides 310 of the second portion of the light guide 110 are each configured to transport a portion of the electromagnetic radiation transported by the first portion of the light guide 110. In some embodiments, for example, the electromagnetic radiation transported by the first portion of the light guide 110 is equally, an equally, and/or approximately equally distributed amongst each of the sub light guides 310.

Figure 8:
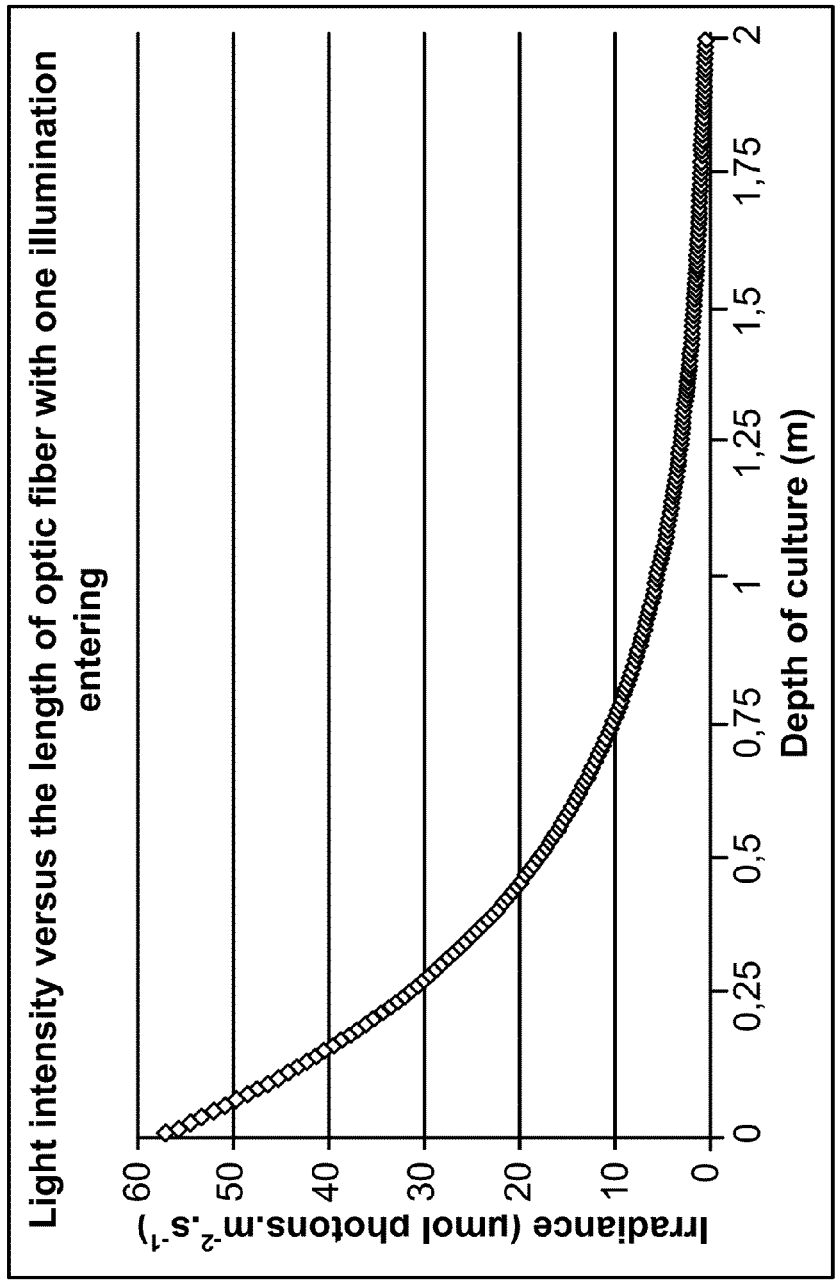
FIG. 8 is a graph illustrating one embodiment of the distribution of irradiance through the PBR as a function of depth along the length of the PBR when electromagnetic energy is provided at one of the top and bottom of the PBR.

In one specific embodiment, the PBR 300 can comprise a 2 m long cylinder with a diameter of 16 cm. In one embodiment, the PBR can include 2,000 sub light guides 310 that each have a diameter of 0.5 mm and a length of 2 m. In some embodiments, the sub light guides 310 can receive electromagnetic energy from first portions of light guide 110 that can connect to one or both of the top and bottom of the PBR 300. In the embodiment in which the first portion of the light guide 110 connects to only one of the top and bottom of the PBR 300, a non-uniform light distribution is created along the length of the PBR 300. This distribution is shown in FIG. 8.

Figure 9:
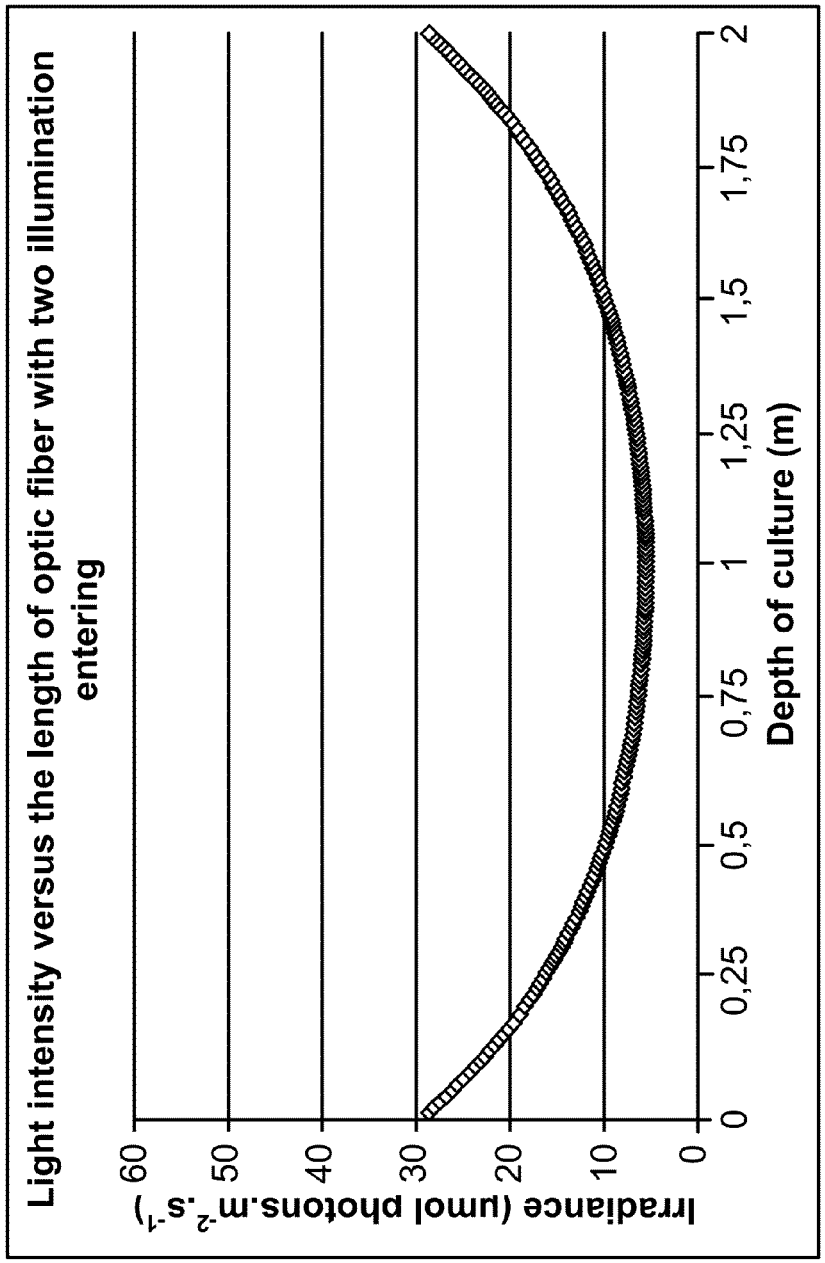
FIG. 9 is a graph illustrating one embodiment of the distribution of irradiance through the PBR as a function of depth along the length of the PBR when electromagnetic energy is provided at both the top and bottom of the PBR.

In the embodiment in which electromagnetic energy is provided to the sub light guides 310 from both top and the bottom of the PBR 300, a non-uniform distribution of illumination along the length of the PBR 300 also occurs, however, this distribution is more homogenous than the distribution of Graph 1. In some embodiments, the distribution of illumination in the PBR 300 is defined as homogenous when the illumination at each longitudinal position of the PBR 300 is above a minimum illumination threshold and when the illumination at each longitudinal position of the PBR 300 does not exceed a maximum threshold. In some embodiments, the minimum and maximum threshold can vary based on the biomass used in the PBR 300 and can be values identifying illumination levels below which growth of the biomass is inhibited, and above which some of the provided light energy is not used by the biomass. The distribution of light along the length of the PBR 300 that occurs when electromagnetic energy is provided from both the top and the bottom of the PBR 300 is shown in FIG. 9.

Figure 4:
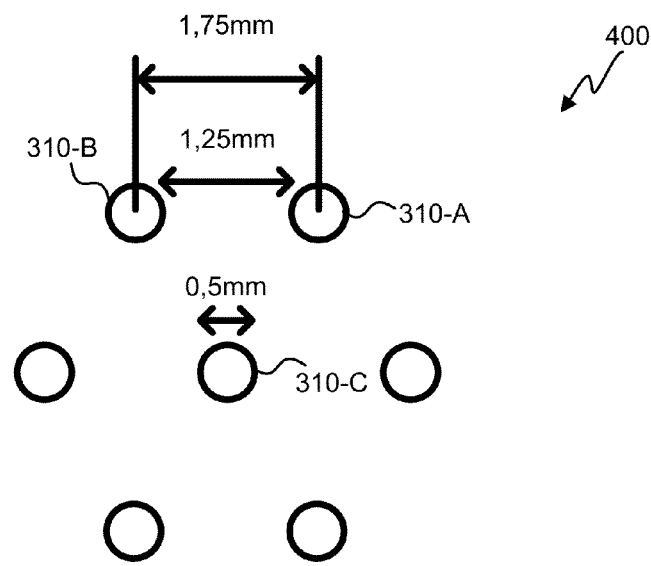
FIG. 4 is a schematic illustration of one embodiment of a light guide distribution pattern.

With reference now to FIG. 4, a schematic illustration of one embodiment of a dispersion array 400 is shown. In some embodiments, for example, the sub light guides 310 can enter into the PBR 300 and be arranged so as to facilitate a desired irradiation of the PBR 300. In one embodiment, for example, the dispersion array 400 is the arrangement of the sub light guides 310 within the PBR 300.

In some embodiments, for example, the dispersion array 400 can be configured to provide a desired amount of illumination to the PBR 300. In some embodiments, for example, the desired amount of illumination of the PBR 300 can be calculated as a ratio of the surface area of the sub light guides 310 within the PBR 300 to the volume of the PBR 300. In some embodiments, for example, the ratio of the surface area of the sub light guides 310 to the volume of the PBR 300 can be indicative of the concentration of biomass that can be maintained and/or grown within the PBR 300. In some embodiments, for example, this ratio can be 10 $m^2/m^3$, 20 $m^2/m^3$, 30 $m^2/m^3$, 50 $m^2/m^3$, 100 $m^2/m^3$, 200 $m^2/m^3$, 500 $m^2/m^3$, 1000 $m^2/m^3$, and/or any other or intermediate number. In one specific embodiment, for example, a ratio 500 $m^2/m^3$ can, for example, support a biomass concentration of up to approximately 20 g/l.

The dispersion array 400 can have uniformly spaced sub light guides 310. In one embodiment, for example, each of the sub light guides 310 can have a diameter of approximately 0.5 mm. In one embodiment, the distance between the circumferential edge of each of the sub light guides 310 can be approximately 1.25 mm, and the distance between the centerline axis of each of the sub light guides 310 can be approximately 1.75 mm. Such distribution pattern is shown in FIG. 4, wherein each of sub light guides 310-A, 310-B, 310-C has a diameter of 0.5 mm and a centerline spacing of 1.75 mm.

Figure 5:
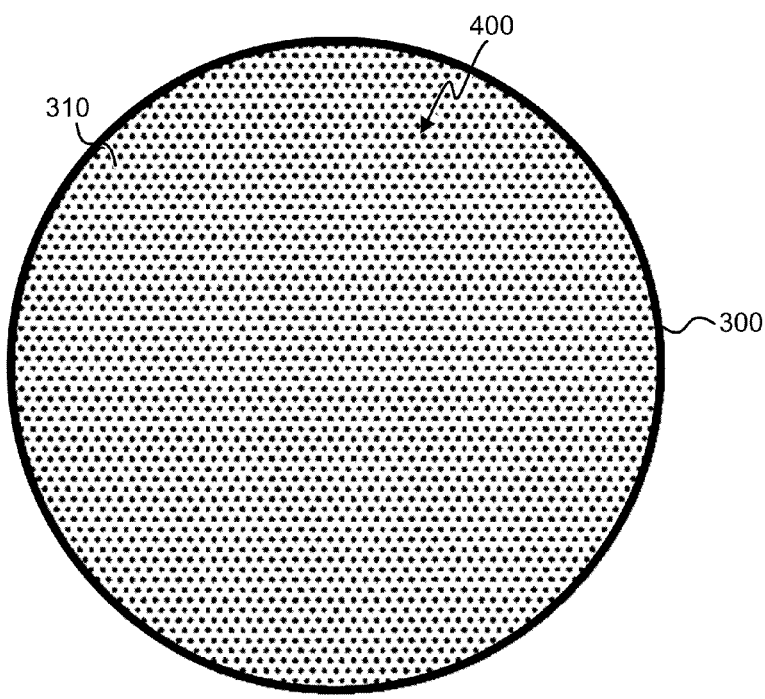
FIG. 5 is a schematic illustration of one embodiment of the light guide distribution pattern within a tank.

With reference now to FIG. 5, a cross-sectional view of one embodiment of the PBR 300 is shown. As seen in FIG. 5, the PBR 300 is filled with the dispersion array 400 comprising a plurality of sub light guides 310. As further seen, the dispersion array 400 comprises a plurality of equally spaced individual sub light guides 310 that are arranged so as to provide a uniform light distribution within each cross-section of the PBR 300 taken perpendicular to the direction of the extension of the sub light guides 310.

Figure 6:
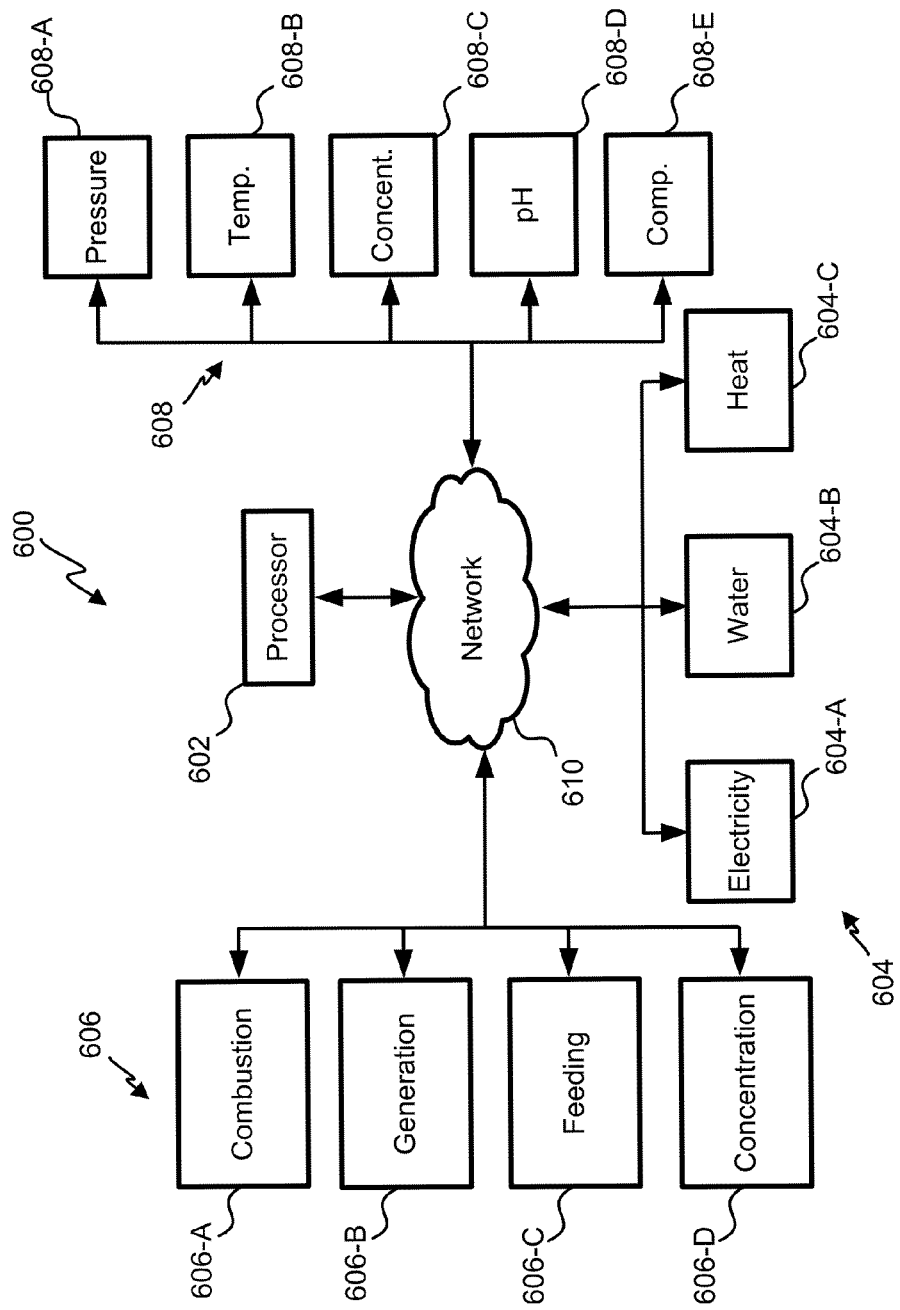
FIG. 6 is a schematic illustration of one embodiment of a control system of a biomass energy generation system.

With reference now to FIG. 6, a schematic illustration of one embodiment of a control system 600 of the biomass energy generation system 100 is shown. In some embodiments, the control system 600 can be configured to monitor and control the operation of the biomass energy generation system 100. In some embodiments, the control system 600 can comprise a plurality of sensors providing information to a processor 602, which processor 602 can, in response to the received information, control other components of the control system 600 to obtain a desired and/or prescribed performance of the biomass energy generation system 100.

The processor 602 can provide instructions to and receive information from the other components of the biomass energy generation system 100. The processor 602 can act according to stored instructions, which stored instructions can be located in memory associated with the processor and/or in other components of the biomass energy generation system 100. The processor 602 can comprise a microprocessor, such as a microprocessor from Intel® or Advanced Micro Devices, Inc.®, or the like.

The control system 600 can comprise demand sensors 604. In some embodiments, the demand sensor 604 can provide an indication of a desired and/or requested output of the biomass energy generation system 100. In some embodiments, this desired and/or requested output can comprise an energy output, a work output, and/or generation of electricity. As depicted in FIG. 6, the demand 604 can comprise an electricity demand sensor 604-A, water demand sensor 604-B, and a heat demand sensor 604-C. In some embodiments, the electricity demand sensor 604-A can provide an indication of a need and/or request for electricity generation, and in some embodiments, can provide an indication of a need and/or request for electricity generation and an indication of a needed and/or requested amount of electricity generation. In some embodiments, the water demand sensor 604-B can provide an indication of a need and/or request for heated water, and in some embodiments, this indication can further include an indication of the desired temperature of the heated water, the amount of heated water, and/or the rate at which the unit water is needed. In some embodiments, the heat demand sensor 604-C can provide an indication of a need and/or request for heat energy and/or heating including, for example, the amount of requested and/or needed heat energy and/or heating and/or the rate of generation of needed and/or requested heat energy and/or heating.

The control system 600 can further comprise control module 606. The control module 606 can correspond to components of the biomass energy generation system 100, and can be configured to control the operation of the corresponding components of the biomass energy generation system 100. In some embodiments, the control module 606 can be used to affect and/or maintain desired environmental conditions within the tank 106, to concentrate biomass, to combust biomass, and/or to generate electricity.

In some embodiments the control module 606 can comprise a combustion module 606-A, a generation module 606-B, a feeding module 606-C, and a concentration module 606-D. In some embodiments, the combustion module 606-A can control the operation of the combustor 116, the generation module 606-B can control the operation of the generator 118 including, for example, the operation of the heat engine, the feeding module 606-C can control the operation of the feeder 120, and the concentration module 606-D can control the operation of the concentrator 114.

In some embodiments, the control system 600 can comprise environmental sensors 608. In some embodiments, the environmental sensors can sense an environmental parameter of the tank 106, of the growth medium 108 and the biomass within the tank 106, and/or of another component of the biomass energy generation system 100. In some embodiments, the environmental sensors 608 can comprise a pressure sensor 608-A that can sense the pressure within the tank 106 and/or within other components of the biomass energy generation system, a temperature sensor 608-B that can sense that temperature of the tank 106 and/or of the biomass and growth medium 108 within the tank 106 and/or of another component of the biomass energy generation system 100, a concentration sensor 608-C that can sense the concentration of the biomass within the growth medium 108 and/or the concentration of one or several chemicals or compounds within the growth medium 108, a pH sensor 608-D that can sense the pH of the growth medium, and a composition sensor 608-E that can sense the composition of the growth medium 108 including, for example, the chemical makeup of the growth medium 108.

In some embodiments, the control system 600 can include a network 610. The network 610 allows communication between the components of the biomass energy generation system 100. The network 610 can comprise any form of connection between the components of the control system 600 including, for example, a wired and/or wireless connection. In some embodiments, the network can connect the components of the control system 600 via for example, a local area network (LAN), a wide area network (WAN), a wired network, wireless network, a telephone network such as, for example, a cellphone network, the Internet, the World Wide Web, or any other desired network. In some embodiments, the network 112 can use any desired communication and/or network protocols.

In some embodiments, the processor 602 can receive a signal from one or several of the environmental sensors 608 indicating an environmental parameter within the biomass energy generation system 100. The signal can indicate, for example, a pressure, a temperature, concentration, a pH, and/or a composition. The processor 602 can compare the received signal to information indicative of a desired and/or specified range for the parameter associated with the received signal, and can determine whether an adjustment to the environmental parameter of the biomass energy generation system 100 should be made. If the processor 602 determines that an adjustment to environmental parameter of the biomass energy generation system 100 should be made, the processor 602 can provide a control signal to one or several of the control modules 606 including, for example, the feeding module 606-C and/or the concentration module 606-D to affect the desired change in the environmental parameter. This control signal can result in the operation of, for example, the theater 120 and/or the concentrator 114.

In some embodiments, for example, the processor 602 can receive a signal from one of the demand sensors 604 indicating a requested and/or needed output of the biomass energy generation system 100. In some embodiments, this request can be for work, heat, hot water, and/or electricity generation. The processor 602 can determine the operation of the biomass energy generation system 100 that will result in the generation of the desired output and can provide control signals to one or several of the control module 606 including, for example, the combustion module 606-A, the generation module 606-B, the feeding module 606-C, and the concentration module 606-D. These control signals can result in the operation of the concentrator 114, the combustor 116, the generator 118, and/or the feeder 120 that can provide the needed and/or requested output of the biomass energy generation system 100.

Figure 7:
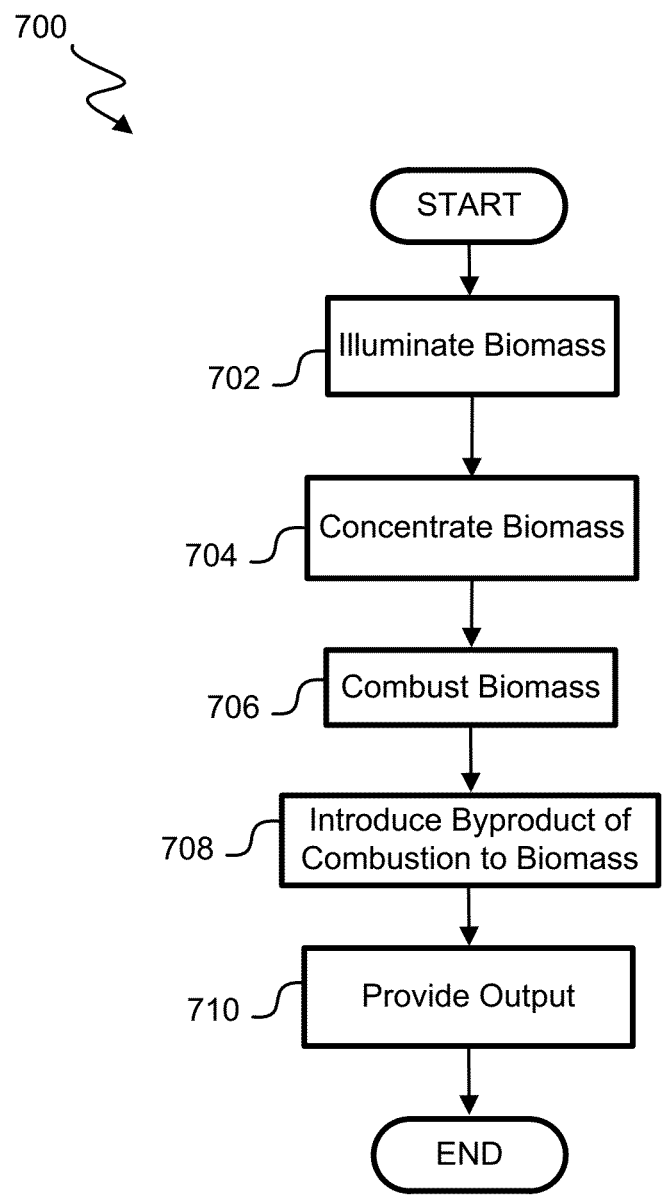
FIG. 7 is a flowchart illustrating one embodiment of a process for operating a biomass energy generation system.

With reference now to FIG. 7, a flowchart illustrating one embodiment of a process 700 for operation of the biomass energy generation system 100 is shown. The process 700 can be performed by the biomass energy generation system 100 and/or the components thereof. In some embodiments, the process 700 can be controlled by the control system 600 of the biomass energy generation system 100.

The process 700 begins at block 702 wherein the biomass is illuminated. In some embodiments, the illumination of the biomass can comprise the collection of electromagnetic energy by the solar collector 104, the transporting of electromagnetic energy from the solar collector 104 to the tank 106 via, for example, the light guide 110, the illumination of the contents of the tank 106, and specifically of the PBR 300 via the dispersion array 400 of sub light guides 310, the providing of growth medium 108 to the biomass to feed and/or nourish and support the growth of the biomass, the sensing of any environmental parameters associated with the biomass, and/or the adjustment of that environmental parameter if it is outside of a desired range. In some embodiments, the illumination of the biomass in block 702 can comprise a growth phase of the biomass which can last until a desired amount and/or concentration of biomass has been achieved.

After the biomass has been illuminated, the process 700 proceeds to block 704 wherein the biomass is concentrated. In some embodiments, the biomass can be received from tank 106, the concentration of the biomass can be measured and/or determined, and, if the concentration of the biomass is not within a desired range, the concentration of the biomass can be altered by the concentrator 114 until a desired and/or specified biomass concentration is achieved. In some embodiments, this can include, for example, diluting the biomass and/or increasing the concentration of the biomass.

After the biomass has been concentrated, the process 700 proceeds to block 706 wherein the biomass is combusted. In some embodiments, the combustion of the biomass can be performed by the combustor 116. In some embodiments, the concentrated biomass can be received from the concentrator 114 and the temperature of the concentrated biomass can be determined. In some embodiments, the temperature of the concentrated biomass can be altered such that the temperature of the concentrated biomass is within a desired and/or specified temperature range. In some embodiments, concentrated biomass can then be provided to the combustor and can be combusted as discussed above.

After the biomass has been combusted, the process 700 proceeds to block 708 wherein a byproduct of the combustion is introduced into the biomass. In some embodiments, for example, the combustion byproducts of the combusted biomass can be collected and can be reintroduced into tank 106. In some embodiments, for example, the combustion byproducts of the combusted biomass can be reintroduced into tank 106 as directed by the control system 600, and specifically by processor 602 of the control system 600. In some embodiments, for example, the combustion byproducts of the combusted biomass can include carbon dioxide, which can be reintroduced into the tank 106 to maintain and/or achieve desired carbon dioxide levels.

After the combustion byproducts of the combusted biomass have been reintroduced into the tank 106, the process 700 proceeds to block 710 wherein the desired output of the biomass energy generation system 100 is provided. In some embodiments, for example, this can include using heat energy generated from the combustion of the biomass to heat water, to heat air, to drive a heat engine, and/or to generate electricity by driving a heat engine. In some embodiments, the outputs of the biomass energy generation system 100 can be controlled by the control system 600, and specifically by the processor 602 of the control system 600.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A growth system comprising:
   a tank having a first side and an opposing second side;
   a luminescent solar collector configured to collect radiation, wherein the luminescent solar collector comprises a luminescent liquid contained between two plates; and
   a plurality of guides configured to transmit radiation collected by the luminescent solar collector, the guides extending into the tank, wherein the guides are configured to create a homogenous distribution of the transmitted radiation in the tank, the plurality of guides comprising:
      a first light guide entering the tank at the first side and extending through the tank from the first side to the second side, wherein the first light guide comprises a first dispersion portion having a sidewall configured to allow the radiation to laterally exit the first light guide; and
      a second light guide entering the tank at the second side and extending through the tank from the second side to the first side, wherein the second light guide comprises a second dispersion portion having a sidewall configured to allow the radiation to laterally exit the second light guide.

2. The growth system of claim 1, wherein the guides comprise:
   a first end;
   a second end; and
   a sidewall extending between the first end and the second end.

3. The growth system of claim 1, wherein the dispersion portion of the first light guide is located proximate to the tank.

4. The growth system of claim 1, wherein the dispersion portion of the first light guide is located inside the tank.

5. The growth system of claim 1, wherein the homogenous distribution of the transmitted radiation in the tank is created by one of: the length of the dispersion portion of the plurality of guides, the number of the plurality of guides, and the spacing of the plurality of guides.

6. The growth system of claim 1, wherein the light guides are configured to receive light from the solar collector and channel the received light to the tank.

7. The growth system of claim 2, wherein the number of the plurality guides creates a homogenous distribution of the transmitted radiation in the tank.

8. The growth system of claim 1, further comprising a solar collector.

9. The growth system of claim 1, wherein the sidewalls of the first dispersion portion and the second dispersion portion are configured to laterally lose 99% of the incident photon flux density in the tank.

10. The growth system of claim 1, wherein the luminescent solar collector comprises alternating parallel plates.

11. The growth system of claim 10, wherein one of the alternating parallel plates comprises a transparent material, and wherein one of the alternating parallel plates comprises a luminescent material.

\* \* \* \* \*